(12) United States Patent
Thompson

(10) Patent No.: US 6,461,302 B1
(45) Date of Patent: Oct. 8, 2002

(54) DEVICE FOR RETRIEVAL OF OVUM

(75) Inventor: Ronald J. Thompson, Fort Thomas, KY (US)

(73) Assignee: MedWorks Corp., Lousville, KY (US)

( * ) Notice: Subject to any disclaimer, the term of this patent is extended or adjusted under 35 U.S.C. 154(b) by 0 days.

(21) Appl. No.: 09/466,383

(22) Filed: Dec. 17, 1999

(51) Int. Cl.[7] .................................................. A61B 8/00
(52) U.S. Cl. ........................................ 600/439; 600/565
(58) Field of Search ............................. 600/33, 34, 35, 600/437–473, 562, 565; 604/27, 44; 435/193, 252.3, 320.1

(56) References Cited

U.S. PATENT DOCUMENTS

| | | | | | |
|---|---|---|---|---|---|
| 4,824,434 | A | * | 4/1989 | Seitz, Jr. ...................... | 604/27 |
| 4,877,033 | A | * | 10/1989 | Seitz, Jr. ...................... | 600/441 |
| 4,982,739 | A | * | 1/1991 | Hemstreet et al. .......... | 128/750 |
| 5,160,319 | A | * | 11/1992 | Emery et al. ................. | 604/27 |
| 5,843,023 | A | * | 12/1998 | Cecchi ......................... | 604/44 |

* cited by examiner

*Primary Examiner*—Marvin M. Lateef
*Assistant Examiner*—Ali M. Imam
(74) *Attorney, Agent, or Firm*—Don Halgren

(57) ABSTRACT

The present invention relates to an ovum retrieval device for retrieving an ovum and follicular fluid from a follicle. The device comprises a housing having a first end wall and a second end, the housing defining a chamber, a movable support arrangement arranged within the chamber, and a needle extending through the first end wall. The needle has a sharpened proximal end disposed within the chamber and a second sharpened distalmost end. A trigger mechanism is connected to the movable support arrangement, and at least one vacuum cartridge is arranged on the support arrangement. Displacement of the support arrangement effects mating of the cartridge and the proximal end of the needle to cause a suction at the second end of the needle to permit an ovum to be withdrawn from a follicle and suctioned into the cartridge prior to further treatment thereof.

20 Claims, 4 Drawing Sheets

DEVICE FOR RETRIEVAL OF OVUM

BACKGROUND OF THE INVENTION

1. Field of the Invention

This invention relates to medical devices, and more particularly to a device for retrieval of ovum and its associated follicular fluid.

2. Prior Art

Fertilization outside of the body is a process which offers women who are having difficulty in conceiving a child, a possible means of having a successful pregnancy. Essentially, an ovum or egg is removed from the perspective mother's ovaries at the time of ovulation and is fertilized in a glass dish or test tube with the sperm from a male donor. This process of fertilization has four distinct components: ovarian hyperstimulation; ultrasound "US" guided transvaginal ovum retrieval; actual in vitro fertilization and embryo maturation; and embryo transfer into the intrauterine cavity. In present practice, an ultrasound guided transvaginal ovum retrieval is accomplished by advancing a very long (36 inch) large bore needle through the posterior vagina, the cul-de-sac and into the peritoneal cavity. The proximal end of the needle is affixed with a fluid trap and is connected to a constant linear pressure suction device via a suction tubing. The suction initially "off" on entry into the peritoneal cavity through the cul-de-sac, because of a large volume of peritoneal fluid. The intent of the ovum retrieval is to isolate the follicular fluid and the ovum contained in it, within the fluid trap without spilling the follicular fluid into the peritoneal fluid and without contaminating the secured specimen with the peritoneal fluid. The fluid trap is blanketed with a small amount of IVF media that acts as a cushion to prevent ovum damage when the ovum is suctioned into the hard fluid trap. The current success rate in ovum retrieval is about a 90%. Some physicians will flush the deflated follicle with IVF media to attempt to increase the yields of the ovum retrieval to over 90%. Some physicians will flush the deflated follicle with IVF media in order to attempt to increase the yield of the ovum retrieval to over 90%.

The current practice of the ovum retrieval however, is cumbersome and requires at least four hands: the surgeon's and an assistant's. The mature follicle has a very friable thin wall, under tension by the pressure of the fluid therewithin. Ovum retrieval is usually scheduled 6 to 8 hours before the anticipated normal follicular rupture, or ovulation. When the sharp IVF needle, typical of the prior art, punctures the follicle, the follicular wall will tear and possibly release the ovum into the surrounding peritoneal fluid. Therefore, it is imperative that the puncture of the follicle with the distal tip of the IVF needle be simultaneous with the initiation of suction at the proximal end of the IVF needle. As the surgeon advances the IVF needle to penetrate the follicle, he/she directs the assistant to initiate suction at the fluid trap. When the follicle is completely deflated, he/she instructs the assistant to discontinue the suction. The fluid cap containing the follicular fluid and the ovum from a single follicle is disconnected from the proximal end of the IVF needle and suction source, and passed to the second assistant. All of these steps are completed as the surgeon controls the sharp needle within the patient's peritoneal cavity as well as the ultrasound in the patient's vagina. A new fluid trap is then attached to the IVF needle and suction is applied to retrieve the next ovum from the next mature follicle. It is typical practice to retrieve six to eight ova sequentially without removing the IVF needle from the peritoneal cavity or without removing the ultrasound probe from the patient's vagina.

It is an object of the present invention to obviate the need of multiple assistants for the surgeon to facilitate ovum retrieval.

It is a further object of the present invention, to provide a method and apparatus that will more safely and more efficiently retrieve multiple ova from a patient.

BRIEF SUMMARY OF THE INVENTION

The present invention comprises of an ovum retrieval apparatus as part of a system for the treatment of fertility conditions which includes the withdrawal of a gamete or egg from an ovary. The ovum retrieval device comprises a housing having a manually workable handle disposed off of one side thereof. The housing has an internal chamber with a forward wall. A long bore needle is arranged through the forward wall and has a proximal end within the chamber of the housing. The proximal end of the needle has a sharpened end thereon.

In one preferred embodiment of the present invention, a vacuum cartridge of generally cylindrical configuration is arranged within the chamber of the housing. The vacuum cartridge is arranged to sit on a slide member. The slide member is movable forwardly and rearwardly on a track arranged within the housing. The track is perpendicular with respect to the forward wall of the retrieval device. A trigger is connectively arranged to the slide member, adjacent to the handle, to permit advancement of the slide member and the vacuum cartridge carried thereon, forward or distally toward the proximal end of the long bore needle secured within the forward wall. The vacuum cartridge has a pierceable membrane on its first end to permit the proximal end of the long bore needle to pierce therethrough. The vacuum cartridge has a second end that may, in one embodiment, have a discharge valve, normally closed, therewithin. The discharge valve is adjacent a discharge port which port is in communication with the internal chamber of the vacuum cartridge. A cartridge-receiving notch may be arranged at the forward end of the slide, to snuggly receive and secure the vacuum cartridge therein. A biased pusher arrangement may be disposed between the perimeter of the first end of the vacuum cartridge and the inside edge of the forward wall of the housing retrieval device. The biased arrangement provides a rearward thrust to the slide member and the vacuum cartridge thereon.

The distal end of the long bore needle has a sharpened tip end thereon. An opening is arranged preferably within the sidewall of the needle adjacent to the sharpened tip end. The opening is in communication with a lumen extending the length of the long bore needle.

In a further embodiment of the present invention, the lumen of the long bore needle may have an arrangement of bumps, internal threads or the like to agitate any fluid passing therealong. In yet a further embodiment the needle may have a further therewithin for the carrying of an ultrasound probe, of the ultrasound probe may be slidably attached to the outerside of the needle shaft, to assist in the guidance and proper placement of the needle tip. In yet a still further preferred embodiment of the present invention, a pressurized rinse-fluid reservoir is arranged in communication with the needle tip, through a further lumen extending therethrough.

In operation of the present invention, the surgeon would pull the trigger on the housing so as to effect a forward motion to the slide member by a lever arranged between the trigger and that slide member. The forward motion of the slide member would effect a piercing of the membrane at the first end of the vacuum cartridge by the proximal end of the long bore needle. As the vacuum cartridge is being pierced, and a vacuum is being applied to the lumen of the long bore needle, the surgeon advances the sharp distal end, into a follicle to penetrate that follicle. The suction created by the piercable vacuum chamber would be non-linear and diminish during the process of the operation. This non-linear suction drawn procedure favors the capture of the ovum as the lumen of the long bore needle fills with follicular fluid, and the negative pressure becomes less within this system. The nonlinear suction may be used to separate the ovum and firmly attended cumulus from other cellular debris. The internal bumps or threads or a cochlear arrangement on the internal surface of the lumen may also be used to agitate the follicle fluid as it enters the ovum, so as to break up clumps of granular cells and strip non-firmly attached cumulus from the ovum. By virtue of the opening disposed on the sidewall of the distal needle tip, a tissue plug may be prevented from contaminating the follicle specimen, as may typically occur with sharp needles with front-tip openings. By virtue of the absence of tissue plugs, and the lack of large granular clumps of cells, this procedure permits the ovum to be separated from the rest of the follicular fluid by a simple gravity through the suspended granular cells. Separation of the ovum by simple gravitational forces would also circumvent the need for an embryologist to visually inspect the entire follicular specimen and to identify separate and isolate the ovum from the follicular fluid.

Once the vacuum cartridge has suctioned-in the ovum and follicular fluid, the trigger may be released to permit the biasing arrangement to push the slide member and vacuum cartridge rearwardly from the forward wall of the housing. The piercable membrane cover on the vacuum cartridge would be self-sealing, and permit the surgeon to remove the vacuum cartridge for further processing. The vacuum cartridge may then be taken to a processing or holding chamber, wherein the discharge port is placed through a penetrable membrane on the holding/processing chamber. The discharge valve may then be opened, to permit the follicular fluid and ovum to drain gravitationally into that processing/holding chamber for further treatment.

A yet further embodiment of the present invention includes the use of multiple vacuum cartridges in a rotary carousel. The carousel would be arranged with a plurality of parallel bores, each containing a vacuum cartridge. Rotation of the carousel to a new unused vacuum cartridge, in alignment with the long bore needle, would permit a sequential penetration of mature follicles for retrieving a plurality of ova thereby. The carousel would be supported rotatively, on a slide member in a manner similar to that of the aforementioned embodiment.

And yet a further embodiment of the present invention, the vacuum cartridges may be placed in a longitudinal manner, on an elongated slide member. Advancement and retraction of that slide member would make the utilization of a first vacuum cartridge, with its subsequent removal and permit rapid linear advancement of a subsequent cartridge forwardly on that slide member into engaging contact with the proximal end of the long bore needle.

Thus it has been shown a unique and efficient manner for the retrieval of an ovum from a follicle and an efficient and economical manner. The present retrieval apparatus permits the puncture of a follicle with the distal tip of the IVF long bore needle simultaneously with the initiation of suction at the proximal end of that needle.

BRIEF DESCRIPTION OF THE DRAWINGS

The objects and advantages of the present invention will become more apparent, when viewed in conjunction with the following drawings in which.

DESCRIPTION OF THE PREFERRED EMBODIMENTS

Figure 1:
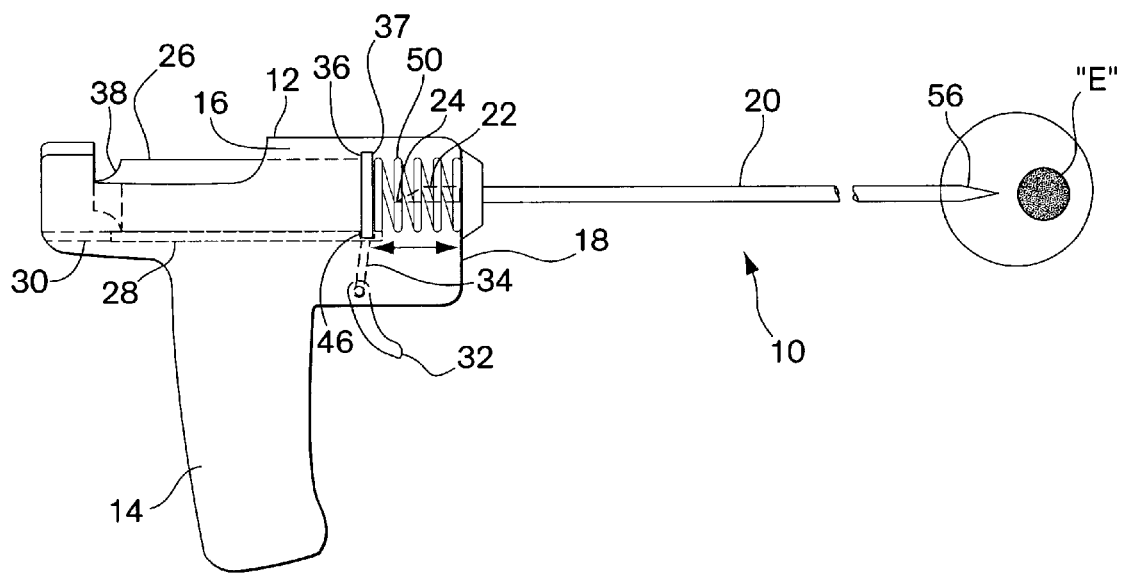
FIG. 1 is a side elevational view of an ovum retrieval apparatus constructed according to the principles of the present invention.

Referring now to the drawings in detail, and particularly to FIG. 1, there is shown the present invention which comprises an ovum retrieval device 10 for the withdrawal of a gamete or egg "E" from an ovary. The ovum retrieval device 10 comprises housing 12 having a manually workable handle 14 disposed off of one side thereof. The housing 12 has an internal chamber 16 with a forward wall 18. A long bore needle 20 is arranged through the forward wall 18 and has a proximal end 22 within the chamber 16 of the housing 12. The proximal end 22 of the needle 20 has a sharpened end 24 thereon.

Figure 3:
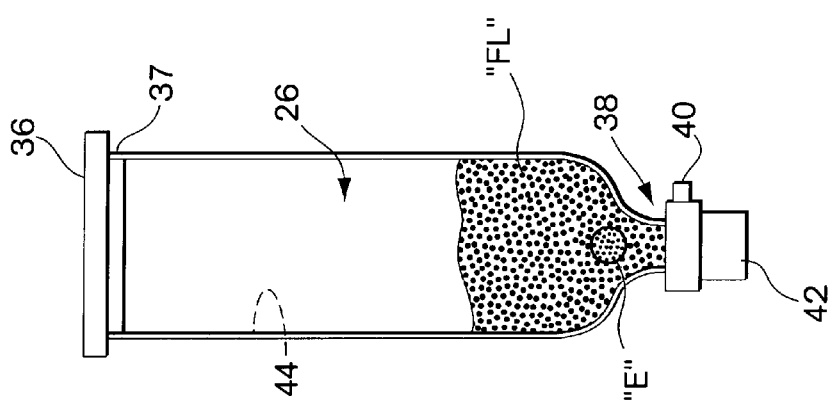
FIG. 3 is a side elevational view of a vacuum cartridge of the present invention.

In one preferred embodiment of the present invention as shown in FIG. 1, a vacuum cartridge 26 of generally cylindrical configuration is arranged within the chamber 16 of the housing 12. The vacuum cartridge 26 is arranged to sit on a slide member 28. The slide member 28 is movable forwardly and rearwardly on a track 30 arranged within the housing 16. The track 30 is perpendicular with respect to the forward wall 18 of the retrieval device 10. A trigger 32 is connectively arranged to the slide member 28 by a lever connector 34, adjacent to the handle 14, to permit advancement of the slide member 28 and the vacuum cartridge 26 carried thereon, forward or distally toward the proximal end 22 of the long bore needle 20 secured within the forward wall 18. The vacuum cartridge 26, as shown more clearly in FIGS. 3, 4 and 5, has a pierceable membrane 36 on its first end 37 to permit the sharpened point 24 on the proximal end 22 of the long bore needle 20 to pierce therethrough. The vacuum cartridge 26 has a second end 38 having a discharge valve 40, normally closed, therewithin. The discharge valve 40 is adjacent a discharge port 42 which port is in communication with the internal chamber 44 of the vacuum cartridge 26. A cartridge-receiving notch 46, as may be seen in FIG. 1, may be arranged at the forward end of the slide 28, to snuggly receive and secure the vacuum cartridge 26 therein. A biased pusher arrangement 50 may be disposed between the perimeter of the first end 37 of the vacuum cartridge 26 and the inside edge of the forward wall 18 of the housing 16 of the retrieval device 10. The biasing arrangement 50 provides a rearward thrust to the slide member 28 and thereby to the vacuum cartridge 26 carried thereon.

Figure 2:
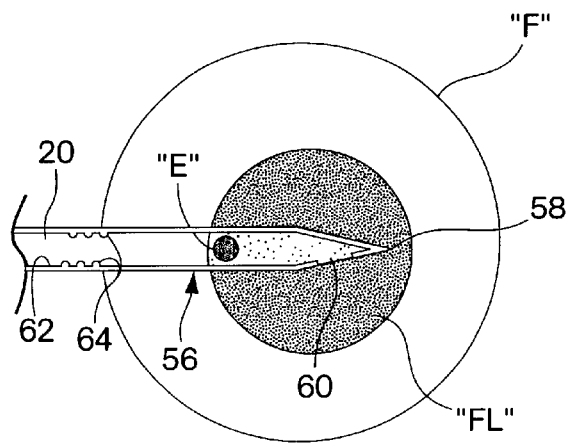
FIG. 2 is an enlarged view of the distal end of the IVF needle shown in FIG. 1, and a follicle penetrating position.

The distal end 56 of the long bore needle 20 has a sharpened tip 58 thereon, as may be seen in FIG. 2. An opening 60 is arranged preferably within the sidewall 62 of the needle 20 adjacent to the sharpened tip end 58. The opening 60 is in communication with a lumen 62 extending the length of the long bore needle 20.

In a further embodiment of the present invention, the lumen 62 of the long bore needle 20 may have an arrangement of bumps, internal threads or the like 64, as shown in FIG. 2, to agitate any fluid suctioned/passing therealong.

In operation of the present invention to initiate suction through the needle 20, the surgeon would pull the trigger 32 on the housing 16 so as to effect a forward motion to the slide member 28 by a lever 34 arranged between the trigger 32 and that slide member 28. The forward motion of the slide member 28 would effect a piercing of the membrane 36 at the first end 37 of the vacuum cartridge 26 by the proximal end 24 of the long bore needle 20. As the vacuum cartridge 26 is being pierced, and a vacuum is being applied to the lumen 62 of the long bore needle 20, the surgeon advances the sharp distal end 58 into a follicle "F" to penetrate that follicle. The suction created by the piercable vacuum chamber 26 would be non-linear and diminish during the process of the operation. This non-linear suction drawn procedure favors the capture of the ovum or egg "E" as the lumen 62 of the long bore needle 20 fills with follicular fluid, and the negative pressure diminishes during the drawing inwardly of the egg into the chamber 44 within this system. The non-linear suction may be used to separate the ovum and firmly attended cumulus from other cellular debris. The internal bumps or threads or a cochlear arrangement on the internal surface of the lumen may also be used to agitate the follicle fluid as it enters the ovum, so as to break up clumps of granular cells and strip non-firmly attached cumulus from the ovum. By virtue of the opening disposed on the sidewall 62 of the distal needle tip 58, a tissue plug may be prevented from contaminating the follicle specimen, as may typically occur with sharp needles with tip openings. By virtue of the absence of tissue plugs, and the lack of large granular clumps of cells, this procedure permits the ovum to be separated from the rest of the follicular fluid by a simple gravity through the suspended granular cells. Separation of the ovum by simple gravitational forces would also circumvent the need for an embryologist to visually inspect the entire follicular specimen and to identify separate and isolate the ovum from the follicular fluid.

Figure 5:
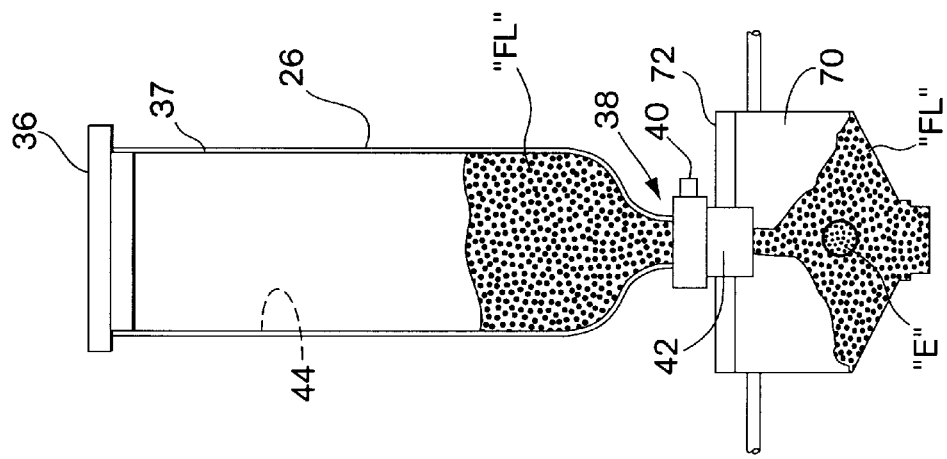
FIG. 5 is a side elevational view of a vacuum cartridge discharges its contents into an incubation chamber through a discharge port.
Figure 4:
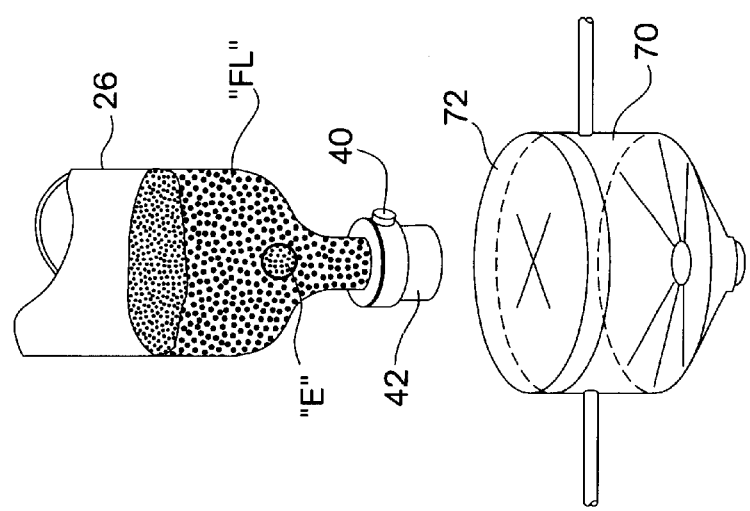
FIG. 4 is a side elevational view of a vacuum cartridge of the present invention juxtaposed against an incubation chamber.

Once the vacuum cartridge 26 has suctioned-in the ovum "E" and follicular fluid "FL", the trigger 32 may be released to permit the biasing arrangement 50 to push the slide member 28 and vacuum cartridge 26 rearwardly from the forward wall 18 of the housing 16. The piercable membrane cover 36 on the vacuum cartridge 26 would be self-sealing, and permit the surgeon to remove the vacuum cartridge 26 for further processing. The vacuum cartridge 26 may then be taken to a holding chamber 70, wherein the discharge port 42 is inserted through a penetrable membrane 72 on that holding/receiving chamber 70, as depicted in FIGS. 4 and 5. The discharge valve 40 may then be opened, to permit the follicular fluid "FL" and ovum "E" to drain gravitationally into that holding chamber.

Figure 6:
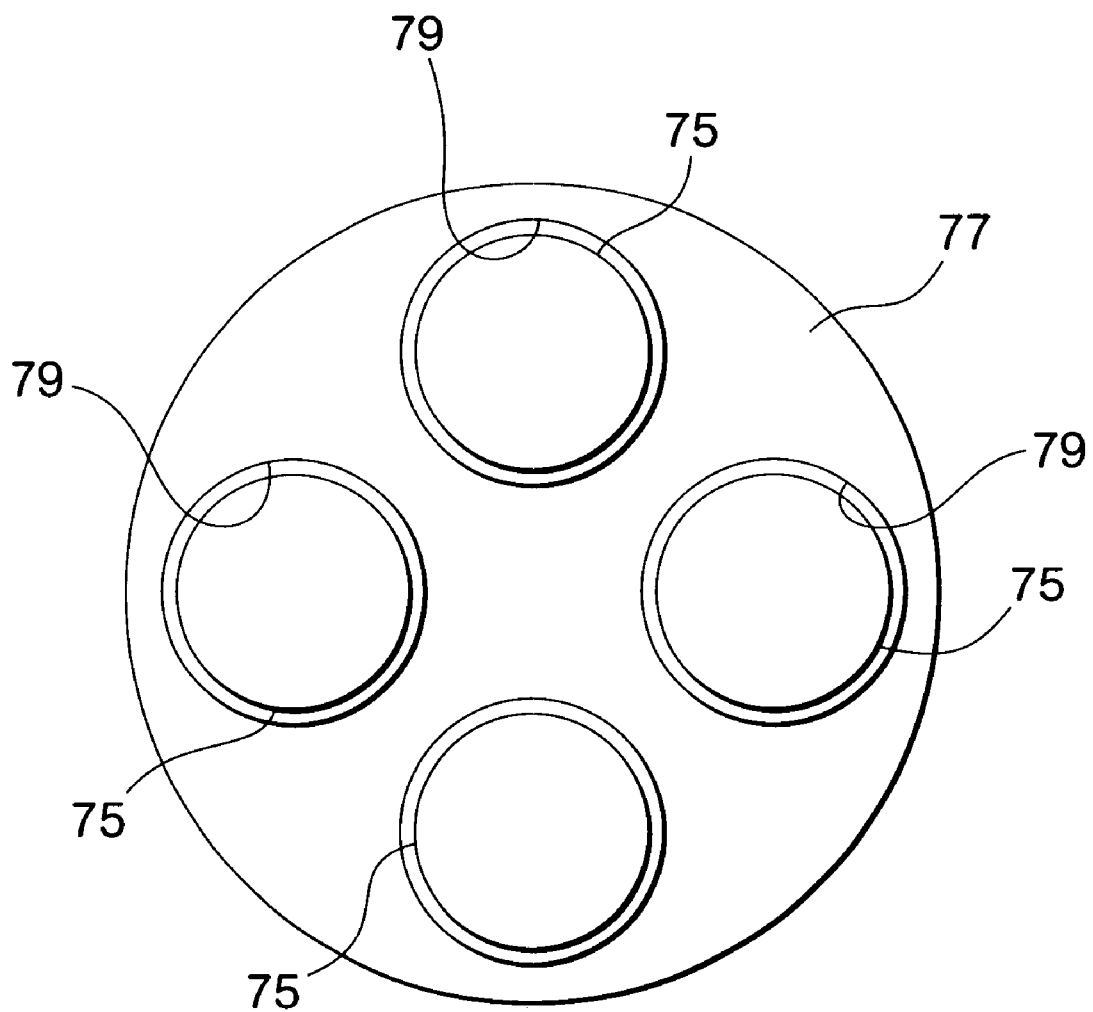
FIG. 6 is an alternative embodiment of a vacuum cartridge arrangement.
Figure 7:
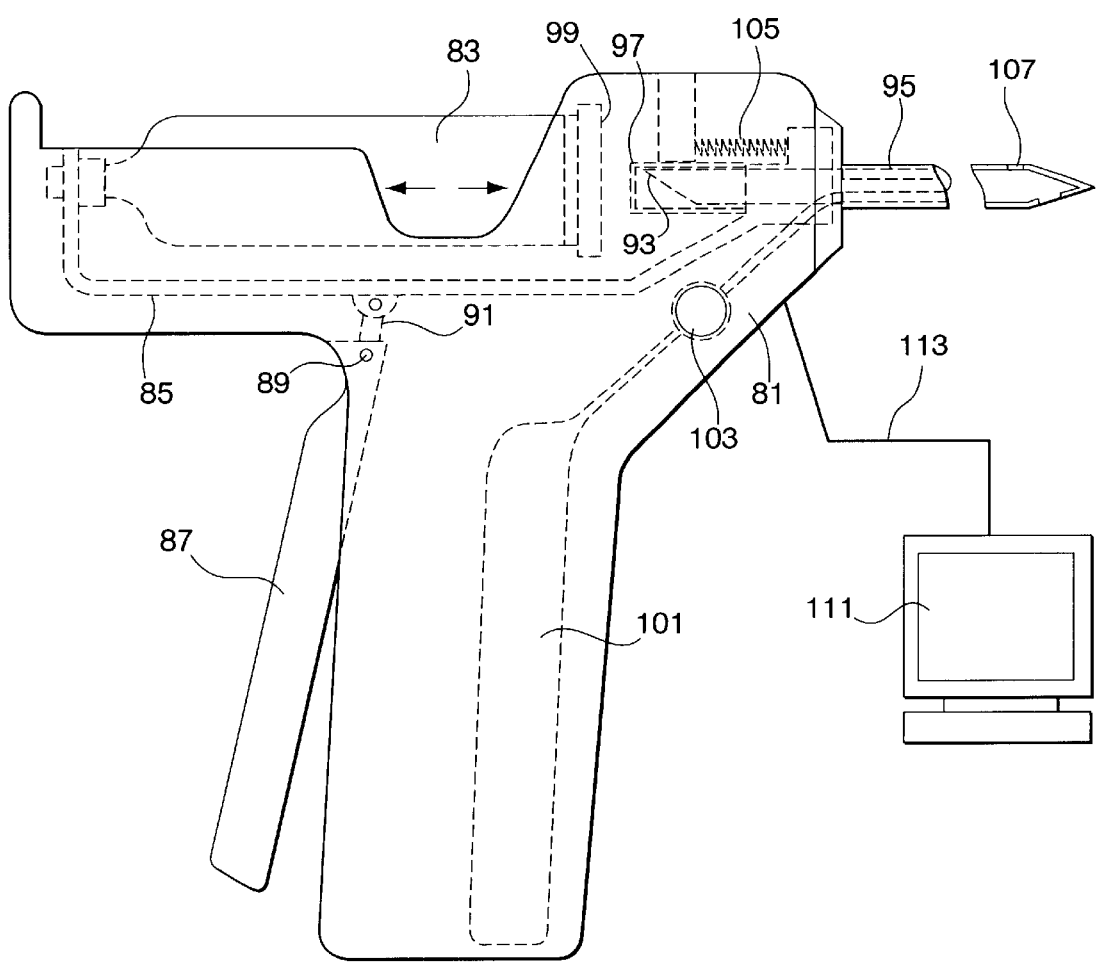
FIG. 7 is a further alternative embodiment of a cartridge support arrangement in a further embodiment of the ovum retrieval apparatus.

A yet further embodiment of the present invention includes the use of multiple vacuum cartridges 75 in a rotary cylinder 77, as shown in FIG. 6. The cylinder 77 would be arranged with a plurality of parallel bores 79, each containing a vacuum cartridge 75. The cylinder 77 may be supported on the slide 28 in a manner similar to the single cartridge 26 shown in FIG. 1. Rotation of the cylinder 77 to a new unused vacuum cartridge 75, in alignment with the long bore needle 20, would permit a sequential penetration of mature follicles for retrieving a plurality of ova thereby.

And yet a further embodiment of the present invention, the vacuum cartridges 26 may be placed in a longitudinal or end-to-end manner, on an elongated slide member, not shown for convenience. Advancement and retraction of that slide member would make the utilization of a first vacuum cartridge, with its subsequent removal and permit rapid linear advancement of a subsequent cartridge forwardly on that slide member into engaging contact with the proximal end of the long bore needle.

In yet a further embodiment of the retrieval apparatus, a housing 81 has a slidably advancable and retractable vacuum cylinder 83 in a support 85. The support 85 is movable by a trigger 87 pivotably attached to the housing 81 by a pin 89. The support 85 is connected to the trigger 87 by a link 91. Squeezing the trigger 87 moves the support 85 and cylinder 83 towards the proximal end 93 of the needle 95. A flexible, piercable sheath 97 is arranged over the proximal end of the needle 95 to protect it until the piercable membrane 99 of the cylinder 83 is pushed onto the proximal end of the needle 95. A pressurized fluid reservoir 101 in this embodiment, is arranged in the housing 81, and is in fluid communication through a separate lumen in the needle 95, with an opening at the distal tip of the needle, not shown for clarity. The fluid may be released from the reservoir 101 by a release valve 103 in the housing 81. A spring 105 is arranged within the housing 81 to bias the cylinder 83 into a retracted, non-pierced orientation, to be pierced again or removed, as the need arises. An ultrasound probe 107 may in yet a further preferred embodiment, be arranged within another lumen in the needle 95. The probe 107 may also be slidably attached to the outside of and in close parallel alignment with the needle 95. The probe 107, connected to a monitor 111 by a cable 113 is used to aid the surgeon in guiding and placing the tip of the needle 95 to the follicle "F".

Thus it has been shown a unique and efficient manner for the retrieval of an ovum from a follicle and an efficient and economical manner. The present retrieval apparatus permits the puncture of a follicle with the distal tip of the IVF long bore needle simultaneously with the initiation of suction at the proximal end of that needle.

I claim:

1. An ovum retrieval device for retrieving an ovum and follicular fluid from a follicle comprising:

a housing having a first end wall and a second end, said housing defining a chamber;

a movable support arrangement arranged within said chamber;

a needle extending through said first end wall, said needle having a sharpened proximal end disposed within said chamber and a second sharpened distalmost end;

a trigger mechanism connected to said movable support arrangement; and at least one vacuum cartridge arranged on said support arrangement whereby displacement of said support arrangement effects mating of said cartridge and said proximal end of said needle to cause a suction at said second end of said needle to permit an ovum to be withdrawn from a follicle and suctioned into said cartridge.

2. The ovum retrieval device as recited in claim 1, wherein said vacuum cartridge has a piercable membrane on a first end thereof, to permit said cartridge to mate with said proximal end of said needle.

3. The ovum retrieval device as recited in claim 2, wherein said housing includes a biasing arrangement disposed between said first wall and said movable support arrangement disposed within said chamber of said housing.

4. The ovum retrieval device as recited in claim 3, wherein said movable support arrangement comprises a slide member slidably disposed upon a track fixedly secured to chamber of said housing.

5. The ovum retrieval device as recited in claim 4, wherein said slide member has a notch arranged therein for securely receiving and holding said vacuum cartridge thereon.

6. The ovum retrieval device as recited in claim 1, wherein said vacuum cartridge has a second end with a discharge port thereon, and a discharge valve disposed in said discharge port to permit contents of said vacuum cartridge to be discharged readily therefrom.

7. The ovum retrieval device as recited in claim 1, including a further receiving chamber for receipt and examination of said contents of said vacuum cartridge.

8. The ovum retrieval device as recited in claim 7, wherein said further receiving chamber has a piercable membrane to permit piercing receipt of said discharge port of said second end of said vacuum cartridge.

9. The ovum retrieval device as recited in claim 1, including an ultrasound probe arranged on said distalmost end of said needle.

10. The ovum retrieval device as recited in claim 1, including a fluid reservoir arranged in communication with said distalmost end of said needle to permit flushing thereof by pressurized fluid.

11. The ovum retrieval device as recited in claim 1, wherein a puncturable sheath is arranged over said proximalmost end of said needle.

12. The ovum retrieval device as recited in claim 1, wherein said needle has a lumen with a distorted internal surface to cause turbulence of follicular fluid passing therethrough.

13. A method of retrieving an ovum from a follicle comprising the steps of:
arranging an elongated needle from a first end wall in a hand manipulable housing, said needle having a pointed distal end and a pointed proximal end;
placing at least one vacuum cartridge onto a movable support within a chamber of said housing, said cartridge having a piercable first end;
controllably piercing a follicle containing an ovum, by said distal end of said elongated needle; and
piercing said vacuum cartridge by said pointed proximal end of said needle to effect suction in said needle and to effect drawing-in of an ovum and follicular fluid into said vacuum cartridge through said needle.

14. The method of retrieving an ovum from a follicle as recited in claim 13, including the step of:
arranging a roughened surface on the lumen on the inside of said needle so as to provide agitation to fluid passing therethrough.

15. The method of retrieving an ovum from a follicle as recited in claim 13, including the step of:
placing a piercable membrane on said first end of said cartridge to permit it to be penetrated by said needle.

16. The method of retrieving an ovum from a follicle as recited in claim 13, including the step of:
attaching an ultrasound probe to said distalmost end of said needle to permit said needle to be properly guided to a follicle.

17. The method of retrieving an ovum from a follicle as recited in claim 16, including the step of:
moving said ultrasound probe with respect to said distalmost end of said needle, to permit operator adjustment and control thereof.

18. The method of retrieving an ovum from a follicle as recited in claim 16, including the step of:
monitoring said distalmost end of said needle by ultrasound tracking during a search for a follicle to be pierced.

19. The method of retrieving an ovum from a follicle as recited in claim 17, including the step of:
flushing said distalmost end of said needle by fluid under pressure to rinse a follicle, said fluid releasably flowing through a lumen within said needle from said reservoir.

20. The method of retrieving an ovum from a follicle as recited in claim 13, including the step of:
pressurizing a fluid in a reservoir in said housing;
arranging said reservoir in fluid communication with said distalmost end of said needle to permit said needle with fluid rinsing capabilities at a follicle during retrieval of an ovum therefrom.

* * * * *